(12) United States Patent
Ptitsyn et al.

(10) Patent No.: US 6,790,647 B2
(45) Date of Patent: Sep. 14, 2004

(54) MUTANT N-ACETYLGLUTAMATE SYNTHASE AND METHOD FOR L-ARGININE PRODUCTION

(75) Inventors: Leonid Romanovich Ptitsyn, Moscow (RU); Irina Borisovna Altman, Moscow (RU); Sergey Vasil'evich Smirnov, Moscow (RU); Yulia Georgievna Rostova, Moscow (RU); Tatyana Abramovna Yampolskaya, Moscow (RU); Tatyana Viktorovna Leonova, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/886,135

(22) Filed: Jun. 22, 2001

(65) Prior Publication Data

US 2003/0148475 A1 Aug. 7, 2003

(30) Foreign Application Priority Data

Jun. 28, 2000 (RU) .......................................... 2000116481
May 15, 2001 (RU) .......................................... 2001112869

(51) Int. Cl.$^7$ ............................. C12N 9/10; C07H 21/04
(52) U.S. Cl. ...................................... 435/193; 536/23.2
(58) Field of Search .......................... 435/193; 536/23.2

(56) References Cited

FOREIGN PATENT DOCUMENTS

EP          1170361 A2 *  9/2002

OTHER PUBLICATIONS

Eckhardt et al. (1975) Molecular and General Genetics, vol. 138, No. 3, pp. 225–232.*
Hayashi et al. (Feb. 28, 2001) "Complete genome sequence of enterohemorrhagic *Escherichia coli* O157:H7 and genomic comparison with a laboratory strain K–12." DNA Research, vol. 8, pp. 11–22.*

R. Cunin, et al., Microbiological Reviews, vol. 50, No. 3, pp. 314–352, XP–001068304, "Biosynthesis and Metabolism of Arginine in Bacteria", Sep. 1986.

K. Brown, et al., Nucleic Acids Research, vol. 15, No. 24, p. 10586, XP–001063143, "Complete Nucleotide Sequence of the *Escherichia coli* Arga Gene", 1987.

V. Sakanyan, et al., Microbiology, vol. 142, No. 1, pp. 99–108, XP–001063142, "Genes and Enzymes of the Acetyl Cycle of Arginine Biosynthesis in *Corynebacterium glutamicum*: Enzyme Evolution in the Early Steps of the Arginine Pathway", 1996.

C. F. Higgins, Annu. Rev. Cell Biol., vol. 8, pp. 67–113, "ABC Transporters: From Microorganisms to Man," 1992.

T. Leisinger, et al., The Journal of Biological Chemistry, vol. 250, No. 5, pp. 1690–1693, "N–Acetylglutamate Synthase of *Escherichia coli* Regulation of synthesis and Activity by Arginine," Mar. 10, 1975.

T. Takagi, et al., J. Biochem, vol. 99, No. 2, pp. 357–364, "Instability of an Arginine–Overproducing Mutant of *Serratia marcescents* and its stabilization," 1986.

B. S. Rajagopal, et al., Applied and Environmental Microbiology, vol. 64, No. 5, pp. 1805–1811, "Use of Inducible Feedback–Resistant N–Acetylglutamate Synthetase (argA) Genes for Enhanced Arginine Biosynthesis by Genetically Engineered *Escherichia coli* K–12 Strains," May 1998.

* cited by examiner

Primary Examiner—Elizabeth Slobodyansky
(74) Attorney, Agent, or Firm—Oblon, Spivak, McClelland, Maier & Neustadt, P.C.

(57) ABSTRACT

L-arginine is produced using a bacterium belonging to the genus Escherichia harboring a mutant N-acetylglutamate synthase in which the amino acid sequence corresponding to positions from 15 to 19 in a wild type N-acetylglutamate synthase is replaced with any one of amino acid sequences of SEQ ID NOS: 1 to 4, and feedback inhibition by L-arginine is desensitized.

12 Claims, 1 Drawing Sheet

MUTANT N-ACETYLGLUTAMATE SYNTHASE AND METHOD FOR L-ARGININE PRODUCTION

BACKGROUND OF THE INVENTION

1. Field of the Invention

The present invention relates to microbiological industry, to the method of L-arginine production and concerns the using of new feedback-resistant mutant enzymes in arginine biosynthesis pathway of *E. coli* arginine-producer strains.

2. Description of the Related Art

The biosynthesis of arginine from glutamate in *E. coli* cells is carried out by a series of reactions initiated by the acetylation of glutamate by N-acetylglutamate synthase (NAGS) encoded by argA. This process is regulated via transcription repression of the arg regulon and by feedback inhibition of NAGS by arginine [Cunin R., et al., *Microbiol. Rev.*, vol.50, p.314–352, 1986]. L-Arginine represses argA expression with a ratio greater than 250 and inhibits NAGS activity (Ki=0.02 mM) [Leisinger T., Haas D., *J. Biol. Chem.*, vol.250, p.1690–1693, 1975]. For enhanced biosynthesis of arginine in *E. coli*, the feedback-resistant (may be referred to as "fbr") NAGS enzymes are required.

The feedback-resistant mutants of enzymes can be obtained by spontaneous, chemical or site-directed mutagenesis.

Some argA fbr mutants were isolated and studied. The *Serratia marcescens* cells carrying the chromosomal fbr argA mutations were unstable and gave rise to argA mutants with reduced activity or with altered affinity for glutamate [Takagi T., et al., *J. Biochem.* vol.99, p.357–364 1986].

The fbr argA genes from the five *E. coli* strains with fbr NAGS were cloned and different single-base substitutions in argA genes were found in each of the fbr NAGS strains and it was revealed that the substitutions cause replacing His-15 with Tyr, Tyr-19 with Cys, Ser-54 with Asn, Arg-58 with His, Gly-287 with Ser and Gln-432 with Arg (Rajagopal B. S. et al., *Appl. Environ. Microbiol.*, 1998, vol.64, No.5, p. 1805–1811).

As a rule, the fbr phenotype of enzyme arises as a result of the replacing the amino acid residue with another in a single or in a few sites of protein sequence and these replacements lead to reducing the activity of enzyme. For example, the replacing of natural Met-256 with 19 other amino acid residues in *E. coli* serine acetyltransferase (SAT) (cysE gene) leads in most cases to fbr phenotype but the mutant SAT proteins do not restore the level of activity of natural SAT (Nakamori S. et al., *AEM*, 64(5):1607–11, 1998).

So, the disadvantage of the mutant enzymes, obtained by these methods, is a reduce in the activity of mutant enzymes as compared to wild type enzymes.

SUMMARY OF THE INVENTION

An object of the present invention is to provide mutant feedback resistant and high active enzymes which play a key role in biosynthesis of arginine by *E. coli*.

In present invention the novel procedure for synthesis a large set of mutant argA genes is proposed by using the full randomization of fragment of argA gene. The simultaneous substitutions of some amino acid residues in fragment of protein sequence, in which the fbr mutation can be localized, can be able to give a mutant proteins with the level of its activity restored near to natural due to more correct restored three dimensional structure of enzyme. Thus the present invention described below has been accomplished.

That is the present invention provides:

(1) A mutant N-acetylglutamate synthase wherein the amino acid sequence corresponding to positions from 15 to 19 in a wild type N-acetylglutamate synthase is replaced with any one of amino acid sequences of SEQ ID NOS: 1 to 4, and feedback inhibition by L-arginine is desensitized;

(2) The mutant N-acetylglutamate synthase according to (1), wherein a wild type N-acetylglutamate synthase is that of *Escherichia coli*.

(3) The mutant N-acetylglutamate synthase according to (1), which includes deletion, substitution, insertion, or addition of one or several amino acids at one or a plurality of positions other than positions from 15 to 19, wherein feedback inhibition by L-arginine is desensitized;

(4) A DNA coding for the mutant N-acetylglutamate synthase as defined in any one of (1) to (3);

(5) A bacterium belonging to the genus Escherichia which is transformed with the DNA as defined in (4) and has an activity to produce L-arginine; and (6) A method for producing L-arginine comprising the steps of cultivating the bacterium as defined in (5) in a medium to produce and accumulate L-arginine in the medium and collecting L-arginine from the medium.

The NAGS having any of fbr mutation as described above may be referred to as "the mutant NAGS", a DNA coding for the mutant NAGS may be referred to as "the mutant argA gene", and a NAGS without mutation may be referred to as "a wild type NAGS".

Hereafter, the present invention will be explained in detail.

<1> Mutant NAGSs and Mutant argA Genes

The mutant NAGSs and the mutant argA genes coding the same were obtained by randomized fragment-directed mutagenesis. To obtain the numerous mutations in argA gene the full randomization of 15-nucleotide fragment of argA gene which codes the region from 15-th to 19-th amino acid residues in protein sequence was carried out. The full randomized 15-nucleotide fragment gives $4^{15}$ or near $10^9$ different DNA sequences which can code $20^5$ different amino acid residues in 5-mer peptide. The likelihood of in frame non-introducing the stop codons in this sequences is equal of about $0.95^5$ or 78%. So, the full randomization of the argA gene fragment coded the peptide from 15-th to 19-th amino acid residues must give approximately 2.5 million different protein sequences with diversity in this peptide fragment of NAGS structure. Subsequent selection and screening of recombinant clones carrying mutant argA genes cloned into expression vector allows to choose the fbr variants of mutant NAGS with different level of its biological activity up to level of activity of derepressed wild-type (wt) NAGS. In the selection, the inventors considered that the strain harboring the mutant argA gene would be obtained by using argD⁻, and prob⁻ or proA⁻ strain, because such a strain cannot produce L-proline due to inhibition of NAGS thereby cannot grow if excess amount of L-arginine exists in a culture medium, but the strain harboring fbr NAGS can grow in a minimal medium because glutamate-semialdehyde, a precursor of L-proline, can be supplied by acetylornithine deacetylase (the argE product) from N-acetylglutamate-semialdehyde, a precursor of L-arginine (Eckhardt T., Leisinger T., *Mol. Gen. Genet.*, vol. 138, p.225–232, 1975). However, the inventors found that it is difficult to obtain fbr NAGS having high activity by the above method as described in the abter-mentioned following Example, and that fbr NAGS having high activity can be obtained by introducing the mutant argA into a wild type strain and selection of a strain which shows delay of cell growth.

The amino acid sequences of the mutant NAGS suitable for fbr phenotype of NAGS were defined by the present invention. Therefore, the mutant NAGS can be obtained based on the sequences by introducing mutations into a wild type argA using ordinary methods. As a wild type argA gene, the argA gene of *E. coli* can be mentioned (GenBank Accession Y00492; the DNA sequence appears as SEQ ID NO: 15 and the corresponding protein sequence appears as SEQ ID NO:16).

The amino acid sequence of positions from 15 to 19 in the mutant NAGS of the present invention is any one of the sequnece of SEQ ID NOS: 1 to 4. The corresponding amino acid sequence of known mutant NAGS, in which tyr at a position 19 is replaced with Cys, and the wild type NAGS of *E. coli* are illustrated in SEQ ID NOS: 5 and 6, respectively. Examples of nucleotide sequence encoding these amino acid sequences are shown in SEQ ID NOS: 7 to 12. Table 1 shows these sequence.

TABLE 1

| Amino acid sequence | SEQ ID NO: | Nucleotide sequence | SEQ ID NO: |
| --- | --- | --- | --- |
| Val Val Trp Arg Ala | 1 | GTAGTATGGCGGGCA | 7 |
| Leu Phe Gly Leu His | 2 | TTGTTCGGATTGCAC | 8 |
| Ser Arg Arg Ser Arg | 3 | TCGCGGCGGTCCAGA | 9 |
| Gly Trp Pro Cys Val | 4 | GGGTGGCCATGCGTG | 10 |
| His Ser Val Pro Cys | 5 | CATTCGGTTCCCTGT | 11 |
| His Ser Val Pro Tyr | 6 | CATTCGGTTCCCTAT | 12 |

The mutant NAGS may including deletion, substitution, insertion, or addition of one or several amino acids at one or a plurality of positions other than 15th to 19th, provided that the NAGS activity, that is an activity to catalyze the reaction of acetylation of L-glutamic acid which produces N-acetylglutamate, is not deteriorated.

The number of "several" amino acids differs depending on the position or the type of amino acid residues in the three dimensional structure of the protein. This is because of the following reason. That is, some amino acids have high homology to one another and the difference in such an amino acid does not greatly affect the three dimensional structure of the protein. Therefore, the mutant NAGS of the present invention may be one which has homology of not less than 30 to 50%, preferably 50 to 70% with respect to the entire amino acid residues for constituting NAGS, and which has the fbr NAGS activity.

In the present invention, "amino acid sequence corresponding to the sequence of positions from 15 to 19" means an amino acid sequence corresponding to the amino acid sequence of positions from 15 to 19 in the amino acid sequence of *E. coli* wild type NAGS. A position of amino acid residue may change. For example, if an amino acid residue is inserted at N-terminus portion, the amino acid residue inherently locates at the position 15 becomes position 16. In such a case, the amino acid residue corresponding to the original position 15 is designated as the amino acid residue at the position 15 in the present invention.

The DNA, which codes for the substantially same protein as the mutant NAGS as described above, may be obtained, for example, by modifying the nucleotide sequence, for example, by means of the site-directed mutagenesis method so that one or more amino acid residues at a specified site involve deletion, substitution, insertion, or addition. DNA modified as described above may be obtained by the conventionally known mutation treatment. The mutation treatment includes a method for treating a DNA containing the mutant argA gene in vitro, for example, with hydroxylamine, and a method for treating a microorganism, for example, a bacterium, belonging to the genus Escherichia harboring the mutant argA gene with ultraviolet irradiation or a mutating agent such as N-methyl-N'-nitro-N-nitrosoquanidine (NTG) and nitrous acid usually used for the mutation treatment.

The substitution, deletion, insertion, or addition of nucleotide as described above also includes mutation which naturally occurs (mutant or variant), for example, on the basis of the individual difference or the difference in species or genus of bacterium which harbors NAGS.

The DNA, which codes for substantially the same protein as the mutant argA gene, is obtained by expressing DNA having mutation as described above in an appropriate cell, and investigating NAGS activity of an expressed product.

Also, the DNA, which codes for substantially the same protein as the mutant NAGS, can be obtained by isolating a DNA which hybridizes with DNA having known argA gene sequence or a probe obtainable therefrom under stringent conditions, and which codes for a protein having the NAGS activity, from a cell harboring the mutant NAGS which is subjected to mutation treatment.

The term "stringent conditions" referred to herein is a condition under which so-called specific hybrid is formed, and non-specific hybrid is not formed. It is difficult to clearly express this condition by using any numerical value. However, for example, the stringent conditions include a condition under which DNAs having high homology, for example, DNAs having homology of not less than 50% with each other are hybridized, and DNAs having homology lower than the above with each other are not hybridized. Alternatively, the stringent condition is exemplified by a condition under which DNA's are hybridized with each other at a salt concentration corresponding to an ordinary condition of washing in Southern hybridization, i.e., 60° C., preferably 65° C., 1×SSC, 0.1% SDS, preferably 0.1×SSC, 0.1% SDS.

The gene, which is hybridizable under the condition as described above, includes those having a stop codon generated within a coding region of the gene, and those having no activity due to mutation of active center. However, such inconveniences can be easily removed by ligating the gene with a commercially available expression vector, and investigating NAGS activity.

<2> Bacterium Belonging to the Genus Escherichia of the Present Invention

The bacterium belonging the genus Escherichia of the present invention is a bacterium belonging to the genus Escherichia to which the mutant argA gene as described above is introduced. A bacterium belonging to the genus Escherichia is exemplified by *E. coli*. The mutant argA gene can be introduced by, for example, transformation of a bacterium belonging to the genus Escherichia with a recombinant DNA comprising a vector which functions in a bacterium belonging to the genus Escherihia and the mutant argA gene. The mutant argA gene can be also introduced by substitution of argA gene on a chromosome with the mutant argA gene.

Vector using for introduction of the mutant argA gene is exemplified by plasmid vectors such as pBR322, pMW118, pUC19 or the like, phage vectors such as 11059, lBF101, M13 mp9 or the like and transposon such as Mu, Tn10, Tn5 or the like.

The introduction of a DNA into a bacterium belonging to the genus Escherichia can be performed, for example, by a method of D. A. Morrison (Methods in Enzymology, 68, 326 (1979)) or a method in which recipient bacterial cell are treated with calcium chloride to increase permeability of DNA (Mandel, M., and Higa, A., *J. Mol. Biol.*, 53, 159, (1970)) and the like.

If the mutant argA gene is introduced into L-arginine-producing bacterium belonging to the genus Escherichia as described above, a produced amount of L-arginine can be increased. Besides, an ability to produce L-arginine may be imparted to a bacterium to which the mutant argA gene is introduced. As the bacterium belonging to the genus Escherichia which has an activity to produce L-arginine is exemplified by *E. coli* 237 strain (VKPM B-7925). The 237 strain has been deposited in Russian National Collection of Industrial Microorganisms (VKPM) under the accession number VKPM B-7925 since Apr. 10, 2000, and transferred to the original deposit to international deposit based on Budapest Treaty, on May 18, 2001.

<3> Method for Producing L-arginine

L-arginine can be efficiently produced by cultivating the bacterium to which the mutant argA gene is introduced and which has an ability to produce L-arginine, in a culture medium, producing and accumulating L-arginine in the medium, and collecting L-arginine from the medium.

In the method of present invention, the cultivation of the bacterium belonging to the genus Escherichia, the collection and purification of L-arginine from the liquid medium may be performed in a manner similar to those of the conventional method for producing L-arginine by fermentation using a bacterium. A medium used in cultivation may be either a synthetic medium or a natural medium, so long as the medium includes a carbon and a nitrogen source and minerals and, if necessary, nutrients which the bacterium used requires for growth in appropriate amount. The carbon source may include various carbohydrates such as glucose and sucrose, and various organic acids, depending on assimilatory ability of the used bacterium. Alcohol including ethanol and glycerol may be used. As the nitrogen source, ammonia, various ammonium salts as ammonium sulfate, other nitrogen compounds such as amines, a natural nitrogen source such as peptone, soybean hydrolyzate and digested fermentative microbe are used. As minerals, monopotassium phosphate, magnesium sulfate, sodium chloride, ferrous sulfate, manganese sulfate, calcium carbonate are used. The cultivation is preferably culture under an aerobic condition such as a shaking, and an aeration and stirring culture. The temperature of culture is usually 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 3-day cultivation leads to the accumulation of L-arginine in the medium.

Collecting L-arginine can be performed by removing solids such as cells from the medium by centrifugation or membrane filtration after cultivation, and then collecting and purifying L-arginine by ion exchange, concentration and crystalline fraction methods and the like.

BEST MODE FOR CARRYING OUT THE INVENTION

Figure 1:
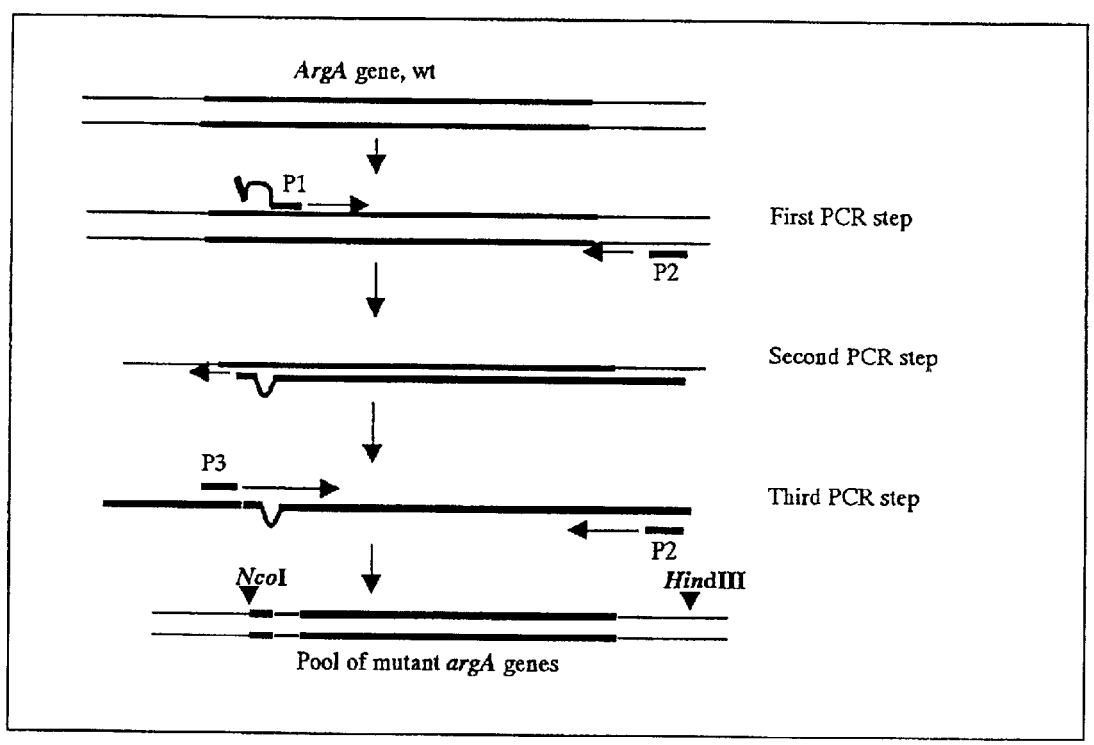
FIG. 1 shows scheme of construction of pool of mutant argA genes.

The present invention will be specifically explained with reference to the following examples.

EXAMPLE 1

<1> The Randomized Fragment-Directed Mutagenesis

The BamHI-SalI chromosomal DNA fragment (2.02 kb) with wt argA gene (SEQ ID: 15) was cloned into plasmid pUC19 (plasmid pUC19-ArgA). PYROBEST™ DNA polymerase used for PCR amplification was obtained from Takara Shuzo Co. (Japan) and is used under the conditions recommended by the supplier.

To construct the pool of mutant argA genes, at the first step the fragment of argA gene coded the sequence from 20-th amino acid residue to the end of NAGS was amplifying (FIG. 1). The plasmid pUC19-ArgA is used as the template, the sense primer P1: 5'-CGAGGGATTCCGCNNNNNNNNNNNNNNNATC AATACCCACCGGG-3' (SEQ ID NO:13), is designed based on the nucleotide sequence of argA and the standard M13 reverse sequence primer is used as a antisense primer P2. The fixed 16-nucleotide 3'-end sequence of primer P1 is homologous to the sequence of argA gene downstream Tyr-19 codon and the fixed 13'-nucleotide 5'-end to the sequence upstream His-15. The homology of 3'-end part of P1 to argA sequence was used to synthesize the 1.75 kbp DNA fragment by using twenty PCR cycles.

100 ng of pUC19-ArgA was added as a template to PCR solution (50 µl) containing each of the two primers (40 pmol). Twenty PCR cycles (94° C. for 0.6 min, 55° C. for 0.5 min, 72° C. for 2 min) is carrying out with a model 2400 DNA thermal cycler (Perkin-Elmer Co., Foster City, Calif.)

At the second step of amplification eight cycles (94° C. for 1 min, 37° C. for 1 min, 72° C. for 0.5 min) is carrying out in which the (−) chain of this fragment is functioning as a "primer" for extension it to get the full gene sequence.

At the third step, the 10 µl aliquot of the reaction mixture is added to a fresh reaction mixture (40 µl) containing 100 pmol of the sense primer P3: 5'-TGCCATGGTAAAGGAACGTAAAACC-3' (SEQ ID NO:14), homologous to 5'-end sequence of argA gene, and primer P2 as antisense, and additional ten cycles (94° C. for 0.5 min, 52° C. for 0.5 min, 72° C. for 2 min) are performed.

The 1.78 kbp DNA fragment coding the pool of mutant variants of full length argA genes is purified by agarose gel electrophoresis, is digested with NcoI (the site which includes the initial ATG codon of argA gene) and HindIII, and then is ligated to the pKK233-2 vector (Pharmacia, Sweden) digested with NcoI and HindIII.

About 150 ng of DNA ligated is used for transformation of E. coli recipient cells in subsequent experiments to give about 2000 recombinant clones in each case.

<2> Isolation of New argA Mutants and Effect of Amino Acid Substitutions in NAGS on Catalytic Properties The plasmid vector pKK 233-2 (Pharmacia, Sweden) was used for cloning and expression of argA gene variants. The E. coli recipient strain was TG1 (supE hsdΔ5 thi Δ(lac-proAB) F'[traD36 proAB+ lacI$^q$ lacZΔM15]) (J. Sambrook et al., *Molecular Cloning*, 1989). The selection TG1 cells carrying the set of recombinant plasmids pKK-argA-random (with argA gene mutants) was carried out on LB agar plates. The delay of cell growth of some mutant clones was observed and this effect was supposed to correlate with production of the active fbr NAGS mutant enzymes. The plasmids from some clones was purified and DNA sequence of 5'-fragments of mutant argA genes was determined by using dideoxy chain termination method (table 2).

To determine the NAGS activity, the arginine auxotroph, strain E. coli B3083 (argA$^-$, metB$^-$) is transformed with these plasmids. The enzymes in the soluble fractions obtained from sonicated recombinant cells is partly purified by ammonium sulfate precipitation and assayed as described below. The NAGS activity of strains carrying plasmids pKK-argA-r11 (3390 nmol/min×mg), pKK-argA-r12 (1220 nmol/min×mg) and pKK-argA-r13 (3120 nmol/min×m g) is significantly higher than the NAGS activity of the strain harboring pKK-argA-r4 (300 nmol/min×mg). The last plasmid carried the mutant argA gene with the same substitution (Y19C) as it was described for most active variant of argA gene with single substitution by Rajagopal B. S. et al. (Rajagopal B. S. et al., *Appl. Environ. Microbiol.*, 1998, v.64, No.5, p. 1805–1811).

Also, the activity of NAGS in strain carrying the plasmid pKK-argA(wt) (wild type argA) is lower than in the case of pKK-argA-r11, -r12 and -r13. The levels of activity of mutant enzymes are approximately the same in presence of 10 mM arginine, while the wild-type enzyme is markedly inhibited by arginine (less than one-tenth). These results indicate that peptide fragment from 15-th to 19-th amino acid residues is responsible for the feedback inhibition of NAGS by L-arginine and for the level of catalytic efficiency of mutant NAGS.

(Enzyme Assay)

The acetyl coenzyme A and all chemicals used were purchased from Sigma Chemical Co., St. Louis, Mo. To determinate NAGS activities, cells E. coli B3083 (argA$^-$, metB$^-$) carrying recombinant plasmids are grown in M9 medium (5 ml) to the late exponential phase, washed with 0.14 M NaCl solution, and resuspended in 2 ml of 40 mM K-phosphate buffer (pH 7.0) with 100 mM KCl. The cells is sonicated and centrifuged. The NAGS containing fractions are precipitated by 5 volumes of saturated $(NH_4)_2SO_4$ and pellets are dissolved in 2 ml of 40 mM K-phosphate buffer (pH 7.0) with 100 mM KCl and 30% (vol/vol) glycerol. The NAGS solution is added to 0.1 ml of reaction mixture (100 mM tris-HCl (pH 8.5), 35 mM KCl, 20 mM L-glutamate, 1.2 mM acetyl coenzyme A) and reaction mixture is incubated at 37° C. for 10 min. The reaction is stopped by adding 0.3 ml of ethanol and reaction mixture is centrifuged. 0.95 ml of 0.24 mM DTNB (5,5-dithio-bis-2-nitrobenzoate) solution is added to supernatant and mixture is incubated for 15 min. The NAGS activity is assayed by measuaring the absorbance at 412 nm.

<3> Isolation of New argA Mutants by Selection in B16-4 (pro$^-$ argD$^-$) Cells The selection of mutant argA (pKK-argA-random) in E. coli B16-4 strain (pro$^-$ argD$^-$) was carried out by the above described procedure. The recombinate clones from agar plates were suspended in M9 medium with L-arginine, and were grown to stationary phase. The aliquot of culture was suspended in the fresh medium and the growth procedure was repeated four times. After that aliquot of culture is plated on M9 argar with 5 mg/ml of L-arginine and 100 μg of ampicillin. The plasmids from some clones were purified, 5'-fragments of mutant argA genes were sequenced and the levels of activity of mutant NAGS were assayed as described above. The 60% of mutants carried the sequence -Gly-Trp-Pro-Cys-Val-(SEQ ID NO: 4) in a mutagenized fragment of enzyme and possessed a weak (about 10 nmol/min× mg) but fbr NAGS activity. Obviously, this mutant protein provides the optimal level of NAGS activity for the growth of pro$^-$ argD- cells in the selection conditions used. So, the conditions of selection are supposed to determine the activity of the mutant NAGS obtained.

TABLE 2

NAGS(ArgA) obtained by randomized fragment-directed mutagenesis

| Clone with Recombinant | Sequence of altered fragment of mutant argA gene | Altered sequence of NAGS (fragment of proteins from 15-th to 19-th a.a.) | NAGS activity, nmol/min × mg* | NAGS activity in the the presence of L-Arg (10 mM), %**. |
|---|---|---|---|---|
| PKKArgA-r11 | GTAGTATGGCGGGCA (SEQ ID NO: 7) | ValValTrpArgAla (SEQ ID NO: 1) | 3390 | 103% |
| PKKArgA-r12 | TTGTTCGGATTGCAC (SEQ ID NO: 8) | LeuPheGlyLeuHis (SEQ ID NO: 2) | 1220 | 100% |
| PKKArgA-r13 | TCGCGGCGGTCCAGA (SEQ ID NO: 9) | SerArgArgSerArg (SEQ ID NO: 3) | 3120 | 107% |
| PKKArgA-32-34, 36, 38.39 | GGGTGGCCATGCGTG (SEQ ID NO: 10) | GlyTrpProCysVal (SEQ ID NO: 4) | 10.3 | 103% |
| PKKArgA-r4 | CATTCGGTTCCCTGT (SEQ ID NO: 11) | HisSerValProCys (SEQ ID NO: 5) | 300 | 91% |

TABLE 2-continued

NAGS(ArgA) obtained by randomized fragment-directed mutagenesis

| Clone with Recombinant | Sequence of altered fragment of mutant argA gene | Altered sequence of NAGS (fragment of proteins from 15-th to 19-th a.a.) | NAGS activity, nmol/min × mg* | NAGS activity in the the presence of L-Arg (10 mM), %**. |
|---|---|---|---|---|
| PKKArgA-wt | CATTCGGTTCCCTAT (SEQ ID NO: 12) | HisSerValProTyr (SEQ ID NO: 6) | 1200 | <10% |

*To total cellular proteins;
**100% stands for activity in the absence of L-Arg.

<4> Production of L-arginine by Using of Mutant argA Genes

The recombinant plasmids pKKArgA-r4, 11, 12, 13 and 32 were digested by BamHI and SalI, and the fragments which contained mutant argA genes under trc promoter were sub-cloned onto low copy plasmid pMW119 (Nippon Gene Co., Tokyo). Resulting plasmids were designated pMADS4, pMADS11, pMADS12, pMADS13 and pMADS32, respectively. These plasmids were introduced into an L-arginine-producing strain E. coli 237 (VKPM B-7925). The L-arginie (Arg) and citrulline (Cit) production of transformants are shown in Table 3. Most of the producer strains with the new mutant NAGS'es give the higher Arg+Cit production than the recipient strain or strain with known Tyr19Cysmutant NAGS (pMADS4).

TABLE 3

Production of L-arginine and citrulline.

| Strain | Arg (g/l) | Cit (g/l) | Arg + Cit (g/l) |
|---|---|---|---|
| 237 | 4.7 | 0 | 4.7 |
| 237/pMADS4 | 8.7 | 0 | 8.7 |
| 237/pMADS11 | 10.0 | 3.0 | 13.0 |
| 237/pMADS12 | 7.6 | 2.6 | 10.2 |
| 237/pMADS13 | 9.1 | 3.7 | 12.8 |
| 237/pMADS32 | 8.2 | 0 | 8.2 |

(The cultivation conditions in test-tube fermentation)

The fermentation medium contained 60 g/l glucose, 25 g/l ammonia sulfate, 2 g/l $KH_2PO_4$, 1 g/l $MgSO_4$, 0.1 mg/l thiamine, 5 g/l yeast extract Difco, 25 g/l chalk, per 1 liter of tap water (pH 7.2). Glucose and chalk were sterilized separately. 2 ml of the medium was placed into test-tubes, inoculated with one loop of the tested microorganisms, and the cultivation was carried out at 32° C. for 3 days with shaking.

What is claimed is:

1. A mutant of N-acetylglutamate synthase wherein amino acid residues corresponding to positions 15 to 19 in the N-acetylglutamate synthase of SEQ ID NO:16 are replaced with any one of amino acid sequences of SEQ ID NOs: 1 to 4, and feedback inhibition by L-arginine is desensitized, wherein the N-acetylglutamate synthase is a protein defined in the following (A) or(B):
    (A) a protein having the amino acid sequence defined in SEQ ID NO: 16; or
    (B) a protein that is encoded by a DNA which hybridizes with a DNA having the nucleotide sequence defined in SEQ ID NO: 15 under stringent conditions, wherein said stringent conditions entail a temperature ranging from 60° C. to 65° C., a salt concentration ranging from 0.1×SSC to 1×SSC, and 0.1% SDS, and wherein said mutant has a N-acetylglutamate synthase activity.

2. The mutant of N-acetylglutamate synthase according to claim 1, where the N-acetylglutamate synthase is that of *Escherichia coli*.

3. The mutant of N-acetylglutamate synthase as defined in claim 1, wherein the N-acetylglutamate synthase has an amino acid sequence defined in SEQ ID NO: 16.

4. The mutant of N-acetylglutamate synthase as defined in claim 3, wherein positions 15 to 19 are replaced with the amino acid sequences of SEQ ID NO: 1.

5. The mutant of N-acetylglutamate synthase as defined in claim 3, wherein positions 15 to 19 are replaced with the amino acid sequences of SEQ ID NO: 2.

6. The mutant of N-acetylglutamate synthase as defined in claim 3, wherein positions 15 to 19 are replaced with the amino acid sequences of SEQ ID NO: 3.

7. The mutant of N-acetylglutamate synthase as defined in claim 3, wherein positions 15 to 19 are replaced with the amino acid sequences of SEQ ID NO: 4.

8. The mutant of N-acetylglutamate synthase as defined in claim 1, wherein the N-acetylglutamate synthase is a protein that is encoded by a DNA which hybridizes with a DNA having the nucleotide sequence defined in SEQ ID NO: 15 under stringent conditions, wherein said stringent conditions entail a temperature ranging from 60° C. to 65° C., a salt concentration ranging from 0.1×SSC to 1×SSC, and 0.1% SDS, and wherein said mutant has a N-acetylglutamate synthase activity.

9. The mutant of N-acetylglutamate synthase as defined in claim 8, wherein positions 15 to 19 are replaced with the amino acid sequences of SEQ ID NO: 1.

10. The mutant of N-acetylglutamate synthase as defined in claim 8, wherein positions 15 to 19 are replaced with the amino acid sequences of SEQ ID NO: 2.

11. The mutant of N-acetylglutamate synthase as defined in claim 8, wherein positions 15 to 19 are replaced with the amino acid sequences of SEQ ID NO: 3.

12. The mutant of N-acetylglutamate synthase as defined in claim 8, wherein positions 15 to 19 are replaced with the amino acid sequences of SEQ ID NO: 4.

* * * * *

SEQUENCE LISTING

```
<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: synthetic peptide

<400> SEQUENCE: 1

Val Val Trp Arg Ala
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic peptide

<400> SEQUENCE: 2

Leu Phe Gly Leu His
```

-continued

<210> SEQ ID NO 3
<211> LENGTH: 5
<212> TYPE: PRT
<213> ORGANISM: Artificial Sequence
<220> FEATURE:
<223> OTHER INFORMATION: synthetic peptide

<400> SEQUENCE: 3

Ser Ala Ala Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic peptide

<400> SEQUENCE: 4

Gly Trp Pro Cys Val
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic peptide

<400> SEQUENCE: 5

His Ser Val Pro Cys
1               5

<210> SEQ ID NO 6
<211> LENGTH: 5
<212> TYPE: PRT
<213> ORGANISM: Escherichia coli

<400> SEQUENCE: 6

His Ser Val Pro Tyr
1               5

<210> SEQ ID NO 7
<211> LENGTH: 15
<212> TYPE: DNA
<213> ORGANISM: Artificial Sequence
<220> FEATURE:
<223> OTHER INFORMATION: synthetic DNA

<400> SEQUENCE: 7
gtagtatggc gggca                                                     15

<210> SEQ ID NO 8
<211> LENGTH: 15
<212> TYPE: DNA
<213> ORGANISM: Artificial Sequence
<220> FEATURE:
<223> OTHER INFORMATION: synthetic DNA

<400> SEQUENCE: 8
ttgttcggat tgcac                                                     15

<210> SEQ ID NO 9
<211> LENGTH: 15

-continued

```
<212> TYPE: DNA
<213> ORGANISM: Artificial Sequence
<220> FEATURE:
<223> OTHER INFORMATION: synthetic DNA

<400> SEQUENCE: 9
tcggcggcgt ccaga                                                     15

<210> SEQ ID NO 10
<211> LENGTH: 15
<212> TYPE: DNA
<213> ORGANISM: Artificial Sequence
<220> FEATURE:
<223> OTHER INFORMATION: synthetic DNA

<400> SEQUENCE: 10
gggtggccat gcgtg                                                     15

<210> SEQ ID NO 11
<211> LENGTH: 15
<212> TYPE: DNA
<213> ORGANISM: Artificial Sequence
<220> FEATURE:
<223> OTHER INFORMATION: synthetic DNA

<400> SEQUENCE: 11
cattcggttc cctgt                                                     15

<210> SEQ ID NO 12
<211> LENGTH: 15
<212> TYPE: DNA
<213> ORGANISM: Escherichia coli

<400> SEQUENCE: 12
cattcggttc cctat                                                     15

<210> SEQ ID NO 13
<211> LENGTH: 44
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (14)..(28)
<223> OTHER INFORMATION: n is a, t, g, or c

<400> SEQUENCE: 13
cgagggattc cgcnnnnnnn nnnnnnnnat caatacccac cggg                     44

<210> SEQ ID NO 14
<211> LENGTH: 25
<212> TYPE: DNA
<213> ORGANISM: Artificial Sequence
<220> FEATURE:
<223> OTHER INFORMATION: synthetic DNA

<400> SEQUENCE: 14
tgccatggta aggaacgta aaacc                                           25

<210> SEQ ID NO 15
<211> LENGTH: 1575
<212> TYPE: DNA
<213> ORGANISM: Escherichia coli
<220> FEATURE:
<221> NAME/KEY: CDS
<222> LOCATION: (244)..(1575)
```

<223> OTHER INFORMATION:

<400> SEQUENCE: 15

| | | | |
|---|---|---|---|
| ggatcctgac atgcctctcc cgagcaaaag aaatctaagc tgtgtaacaa gtaaacgact | 60 |
| aatttgaccg gtttcaaaag cgaaagacgc ataatctgtc atctaataaa cggtaaacat | 120 |
| tcttttttata ttcacggcat tactgataaa aaagtcgctc tcgcataaaa tttacacttg | 180 |
| caccctgcga aaaacagaa taaaaataca ctaatttcga ataatcatgc aaagaggtgt | 240 |

```
gcc gtg gta aag gaa cgt aaa acc gag ttg gtc gag gga ttc cgc cat        288
Val Val Lys Glu Arg Lys Thr Glu Leu Val Glu Gly Phe Arg His
  1               5                  10                  15 tcg gtt ccc tat atc aat acc cac cgg gga aaa acg ttt gtc atc atg        336
Ser Val Pro Tyr Ile Asn Thr His Arg Gly Lys Thr Phe Val Ile Met
             20                  25                  30 ctc ggc ggt gaa gcc att gag cat gag aat ttc tcc agt atc gtt aat        384
Leu Gly Gly Glu Ala Ile Glu His Glu Asn Phe Ser Ser Ile Val Asn
         35                  40                  45 gat atc ggg ttg ttg cac agc ctc ggc atc cgt ctg gtg gtg gtc tat        432
Asp Ile Gly Leu Leu His Ser Leu Gly Ile Arg Leu Val Val Val Tyr
     50                  55                  60 ggc gca cgt ccg cag atc gac gca aat ctg gct gcg cat cac cac gaa        480
Gly Ala Arg Pro Gln Ile Asp Ala Asn Leu Ala Ala His His His Glu
 65                  70                  75 ccg ctg tat cac aag aat ata cgt gtg acc gac gcc aaa aca ctg gaa        528
Pro Leu Tyr His Lys Asn Ile Arg Val Thr Asp Ala Lys Thr Leu Glu
 80                  85                  90                  95 ctg gtg aag cag gct gcg gga aca ttg caa ctg gat att act gct cgc        576
Leu Val Lys Gln Ala Ala Gly Thr Leu Gln Leu Asp Ile Thr Ala Arg
                100                 105                 110 ctg tcg atg agt ctc aat aac acg ccg ctg cag ggc gcg cat atc aac        624
Leu Ser Met Ser Leu Asn Asn Thr Pro Leu Gln Gly Ala His Ile Asn
            115                 120                 125 gtc gtc agt ggc aat ttt att att gcc cag ccg ctg ggc gtc gat gac        672
Val Val Ser Gly Asn Phe Ile Ile Ala Gln Pro Leu Gly Val Asp Asp
        130                 135                 140 ggc gtg gat tac tgc cat agc ggg cgt atc cgg cgg att gat gaa gac        720
Gly Val Asp Tyr Cys His Ser Gly Arg Ile Arg Arg Ile Asp Glu Asp
    145                 150                 155 gcg atc cat cgt caa ctg gac agc ggt gca ata gtg cta atg ggg ccg        768
Ala Ile His Arg Gln Leu Asp Ser Gly Ala Ile Val Leu Met Gly Pro
160                 165                 170                 175 gtc gct gtt tca gtc act ggc gag agc ttt aac ctg acc tcg gaa gag        816
Val Ala Val Ser Val Thr Gly Glu Ser Phe Asn Leu Thr Ser Glu Glu
                180                 185                 190 att gcc act caa ctg gcc atc aaa ctg aaa gct gaa aag atg att ggt        864
Ile Ala Thr Gln Leu Ala Ile Lys Leu Lys Ala Glu Lys Met Ile Gly
            195                 200                 205 ttt tgc tct tcc cag ggc gtc act aat gac gac ggt gat att gtc tcc        912
Phe Cys Ser Ser Gln Gly Val Thr Asn Asp Asp Gly Asp Ile Val Ser
        210                 215                 220 gaa ctt ttc cct aac gaa gcg caa gcg cgg gta gaa gcc cag gaa gag        960
Glu Leu Phe Pro Asn Glu Ala Gln Ala Arg Val Glu Ala Gln Glu Glu
    225                 230                 235 aaa ggc gat tac aac tcc ggt acg gtg cgc ttt ttg cgt ggc gca gtg       1008
Lys Gly Asp Tyr Asn Ser Gly Thr Val Arg Phe Leu Arg Gly Ala Val
240                 245                 250                 255 aaa gcc tgc cgc agc ggc gtg cgt cgc tgt cat tta atc agt tat cag       1056
Lys Ala Cys Arg Ser Gly Val Arg Arg Cys His Leu Ile Ser Tyr Gln
                260                 265                 270
```

-continued

```
gaa gat ggc gcg ctg ttg caa gag ttg ttc tca cgc gac ggt atc ggt      1104
Glu Asp Gly Ala Leu Leu Gln Glu Leu Phe Ser Arg Asp Gly Ile Gly
        275                 280                 285 acg cag att gtg atg gaa agc gcc gag cag att cgt cgc gca aca atc      1152
Thr Gln Ile Val Met Glu Ser Ala Glu Gln Ile Arg Arg Ala Thr Ile
    290                 295                 300 aac gat att ggc ggt att ctg gag ttg att cgc cca ctg gag cag caa      1200
Asn Asp Ile Gly Gly Ile Leu Glu Leu Ile Arg Pro Leu Glu Gln Gln
305                 310                 315 ggt att ctg gta cgc cgt tct cgc gag cag ctg gag atg gaa atc gac      1248
Gly Ile Leu Val Arg Arg Ser Arg Glu Gln Leu Glu Met Glu Ile Asp
320                 325                 330                 335 aaa ttc acc att att cag cgc gat aac acg act att gcc tgc gcc gcg      1296
Lys Phe Thr Ile Ile Gln Arg Asp Asn Thr Thr Ile Ala Cys Ala Ala
            340                 345                 350 ctc tat ccg ttc ccg gaa gag aag att ggg gaa atg gcc tgt gtg gca      1344
Leu Tyr Pro Phe Pro Glu Glu Lys Ile Gly Glu Met Ala Cys Val Ala
            355                 360                 365 gtt cac ccg gat tac cgc agt tca tca agg ggt gaa gtt ctg ctg gaa      1392
Val His Pro Asp Tyr Arg Ser Ser Ser Arg Gly Glu Val Leu Leu Glu
        370                 375                 380 cgc att gcc gct cag gct aag cag agc ggc tta agc aaa ttg ttt gtg      1440
Arg Ile Ala Ala Gln Ala Lys Gln Ser Gly Leu Ser Lys Leu Phe Val
385                 390                 395 ctg acc acg cgc agt att cac tgg ttc cag gaa cgt gga ttt acc cca      1488
Leu Thr Thr Arg Ser Ile His Trp Phe Gln Glu Arg Gly Phe Thr Pro
400                 405                 410                 415 gtg gat att gat tta ctg ccc gag agc aaa aag cag ttg tac aac tac      1536
Val Asp Ile Asp Leu Leu Pro Glu Ser Lys Lys Gln Leu Tyr Asn Tyr
            420                 425                 430 cag cgt aaa tcc aaa gtg ttg atg gcg gat tta ggg taa                  1575
Gln Arg Lys Ser Lys Val Leu Met Ala Asp Leu Gly
                435                 440
```

<210> SEQ ID NO 16
<211> LENGTH: 443
<212> TYPE: PRT
<213> ORGANISM: Escherichia coli

<400> SEQUENCE: 16

```
Val Val Lys Glu Arg Lys Thr Glu Leu Val Glu Gly Phe Arg His Ser
1               5                   10                  15

Val Pro Tyr Ile Asn Thr His Arg Gly Lys Thr Phe Val Ile Met Leu
            20                  25                  30

Gly Gly Glu Ala Ile Glu His Glu Asn Phe Ser Ser Ile Val Asn Asp
        35                  40                  45

Ile Gly Leu Leu His Ser Leu Gly Ile Arg Leu Val Val Tyr Gly
    50                  55                  60

Ala Arg Pro Gln Ile Asp Ala Asn Leu Ala Ala His His Glu Pro
65                  70                  75                  80

Leu Tyr His Lys Asn Ile Arg Val Thr Asp Ala Lys Thr Leu Glu Leu
                85                  90                  95

Val Lys Gln Ala Ala Gly Thr Leu Gln Leu Asp Ile Thr Ala Arg Leu
            100                 105                 110

Ser Met Ser Leu Asn Asn Thr Pro Leu Gln Gly Ala His Ile Asn Val
        115                 120                 125

Val Ser Gly Asn Phe Ile Ile Ala Gln Pro Leu Gly Val Asp Asp Gly
    130                 135                 140
```

-continued

```
Val Asp Tyr Cys His Ser Gly Arg Ile Arg Ile Asp Glu Asp Ala
145                 150                 155                 160

Ile His Arg Gln Leu Asp Ser Gly Ala Ile Val Leu Met Gly Pro Val
                165                 170                 175

Ala Val Ser Val Thr Gly Glu Ser Phe Asn Leu Thr Ser Glu Glu Ile
                180                 185                 190

Ala Thr Gln Leu Ala Ile Lys Leu Lys Ala Glu Lys Met Ile Gly Phe
            195                 200                 205

Cys Ser Ser Gln Gly Val Thr Asn Asp Asp Gly Asp Ile Val Ser Glu
        210                 215                 220

Leu Phe Pro Asn Glu Ala Gln Ala Arg Val Glu Ala Gln Glu Glu Lys
225                 230                 235                 240

Gly Asp Tyr Asn Ser Gly Thr Val Arg Phe Leu Arg Gly Ala Val Lys
                245                 250                 255

Ala Cys Arg Ser Gly Val Arg Arg Cys His Leu Ile Ser Tyr Gln Glu
                260                 265                 270

Asp Gly Ala Leu Leu Gln Glu Leu Phe Ser Arg Asp Gly Ile Gly Thr
            275                 280                 285

Gln Ile Val Met Glu Ser Ala Glu Gln Ile Arg Arg Ala Thr Ile Asn
    290                 295                 300

Asp Ile Gly Gly Ile Leu Glu Leu Ile Arg Pro Leu Glu Gln Gln Gly
305                 310                 315                 320

Ile Leu Val Arg Arg Ser Arg Glu Gln Leu Glu Met Glu Ile Asp Lys
                325                 330                 335

Phe Thr Ile Ile Gln Arg Asp Asn Thr Thr Ile Ala Cys Ala Ala Leu
            340                 345                 350

Tyr Pro Phe Pro Glu Glu Lys Ile Gly Glu Met Ala Cys Val Ala Val
            355                 360                 365

His Pro Asp Tyr Arg Ser Ser Ser Arg Gly Glu Val Leu Leu Glu Arg
    370                 375                 380

Ile Ala Ala Gln Ala Lys Gln Ser Gly Leu Ser Lys Leu Phe Val Leu
385                 390                 395                 400

Thr Thr Arg Ser Ile His Trp Phe Gln Glu Arg Gly Phe Thr Pro Val
                405                 410                 415

Asp Ile Asp Leu Leu Pro Glu Ser Lys Lys Gln Leu Tyr Asn Tyr Gln
            420                 425                 430

Arg Lys Ser Lys Val Leu Met Ala Asp Leu Gly
            435                 440
```